United States Patent [19]

Walder-Utz et al.

[11] Patent Number: 5,730,746
[45] Date of Patent: Mar. 24, 1998

[54] DEVICE FOR POSITIONING SKIN CLIPS

[75] Inventors: Alice Walder-Utz, Zurich; Werner Fritz Dubach, Maur, both of Switzerland

[73] Assignee: Createchnic AG, Dietlikon, Switzerland

[21] Appl. No.: 718,466
[22] PCT Filed: Apr. 4, 1995
[86] PCT No.: PCT/CH95/00075
§ 371 Date: Sep. 27, 1996
§ 102(e) Date: Sep. 27, 1996
[87] PCT Pub. No.: WO95/27442
PCT Pub. Date: Oct. 19, 1995

[30] Foreign Application Priority Data

Apr. 8, 1994 [CH] Switzerland ............... 1053/94

[51] Int. Cl.$^6$ ...................................... A61B 17/04
[52] U.S. Cl. ............................................ 606/143
[58] Field of Search ........................... 606/143, 142

[56] References Cited

U.S. PATENT DOCUMENTS 4,671,278  6/1987  Chin ........................ 606/143

FOREIGN PATENT DOCUMENTS

| 0090484 | 10/1983 | European Pat. Off. |
| 0469524 | 2/1992 | European Pat. Off. |
| WO 8302887 | 9/1983 | WIPO |
| WO 8801487 | 3/1988 | WIPO |
| WO 9309721 | 5/1993 | WIPO |

*Primary Examiner*—Gary Jackson
*Attorney, Agent, or Firm*—Weingarten, Schurgin, Gagnebin & Hayes LLP

[57] ABSTRACT

The invention concerns a device for positioning skin clips which consists of a housing (1) made from two half-shells (10, 11), for example. The housing (1) accommodates a magazine (2) comprising two strips (20) and resilient retaining plates (21) secured thereto. Arranged in the center between the latter is a rod-shaped delivery device (3) which can be moved up and down by means of an actuating lever (5) co-operating with a restoring spring (6). The skin clips (4) are arranged in a row on the rod-shaped delivery device (3) and are prevented by saw-teeth (30) thereon from sliding upwards on the delivery device (3) as it moves downwards. At the same time, the resilient retaining plates (21) ensure that the spring clips remain in position when the rod-shaped delivery device (3) moves upwards. The rod-shaped delivery device (3) comprises at its end a widening (31) by means of which the lowermost skin clip is held spread apart before it is stripped off.

8 Claims, 2 Drawing Sheets

DEVICE FOR POSITIONING SKIN CLIPS

FIELD OF THE INVENTION

This invention concerns a device for positioning skin clips from a magazine in its housing.

BACKGROUND OF THE INVENTION

Extremely simple, spring-action skin clips that clip together the edges of a wound are known from U.S. Pat. No. 3,601,127 and FR-A419 096. The first clips mentioned consist of two metal webs, whose cross section is roughly U-shaped, which are connected to one another by an elastic strip. The edges of the wound are held by claw-type tips. The edges of the wound are perforated and thus associated infections and traumatic reactions cannot be ruled out. The second type of surgical clip mentioned consists of a single punched, curved part made of stainless spring steel, in which the edges of the wound are pinched together and turned up and retaining edges prevent the edges of the wound from slipping out. Medically, this solution is not optimal either, since here again the edges of the wound in the turned-up area can be perforated, and these infections are not accessible to visual control. Any infections that occur are thus discovered only relatively late.

A similar type of surgical clip is known from U.S. Pat. No. 4,217,902. This surgical clip has means whereby it can be grasped with a forceps and positioned. The surgical clips mentioned above are usually positioned manually by surgeons. The most comfortable skin clip is the one developed by the applicant in EP-B-224 500. Here, the edges of the wound are pressed against one another between two wavy pressure edges. Here there is no perforation. The appearance of the remaining scar is consequently free of puncture points, like those that occur in sutured wound closings or along the edges of wounds that were held together by means of the above-mentioned wound clips or by means of the known staples.

Despite the fact that the staples mentioned are pressed relatively deeply into the skin on both sides of the wound and consequently traumatic conditions can often be found in the wound area and the risk of infection is also relatively high, these staple systems have become very widespread. This is due to the fact that they are especially user-friendly. They come in disposable devices that consist of a housing in which a magazine with a fixed predetermined number of staples is placed. Once the staple-shaped skin clips are positioned and the magazine is empty or the wound closing complete, the whole device, including any unused skin staples, is thrown away.

The task of this invention is to create for the first time a device for positioning skin clips from a magazine in its housing, wherein the skin clips are the type mentioned at the beginning. This requires a completely different design to store and dispense the skin clips compared to the known devices.

The above-mentioned task is solved by a device for positioning skin clips from a magazine placed in its housing having at least one feed ratchet acting on all the skin clips held in the magazine. All the skin clips are advanced at the same time, and the skin clip in the lowest position can be put into a spread position. The feed ratchet has the shape of a sword-like rod designed with saw-teeth on both sides, whose lowest end is widened in the direction in which the skin clips are dispensed. The magazine has a backstop ratchet with spring retaining plates on both sides, which are next to all the skin clips in the magazine on both sides and let it move in only one direction. Since the skin clips used here do not have just the design of curved wire sections, as is the case with staples, they cannot be arranged next to one another, as is the case with devices for applying staples, but must be arranged over one another in stacked form.

Advantageous forms of embodiment of the object of the invention are claimed in the claims, and their meaning and action are explained in the description that follows.

DESCRIPTION OF THE DRAWINGS

The enclosed drawings show a preferred example of embodiment of the object of the invention and explain it in the description, with reference to the figures.

DETAILED DESCRIPTION OF THE INVENTION

Figure 1:
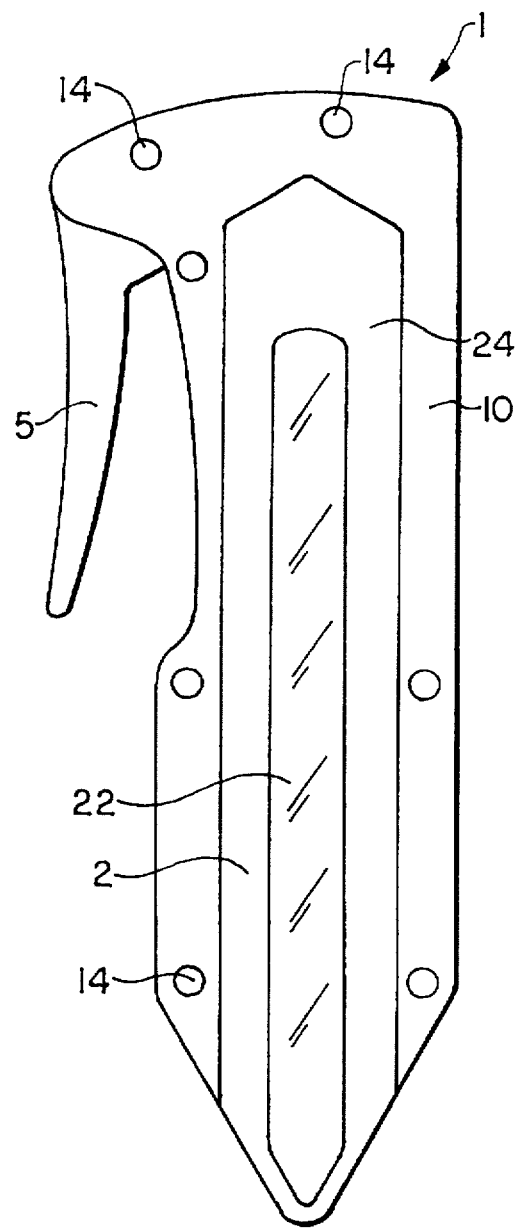
FIG. 1 shows a front view of the device in the invention with a changeable magazine.

FIG. 1 shows a preferred form of embodiment of the device for positioning skin clips in roughly the natural size. The whole housing is marked number 1. In this form of embodiment, it consists of two housing shells, namely the front housing shell 10 and the back housing shell 11. Both housing shells overlap and are connected at connecting points 14. These connecting points 14 can be screw, rivet or weld connections. When mass produced, the pure connectors used widely in plastics technology will be chosen, which combine to produce an interlocking, snap-on connection. In this way, the two half shells 10 and 11 need only be placed one over the other and pressed together. When the device is in the closed state, one can still see an activating lever 5 and the magazine 2. The magazine 2 has at least a front cover with a see-through window 22, which permits visual control of the skin clips still available. In principle, the whole magazine 2 can, of course, be made of transparent material.

Preferably, it is made of a high-quality plastic approved for medical purposes like skin clips.

Figure 2:
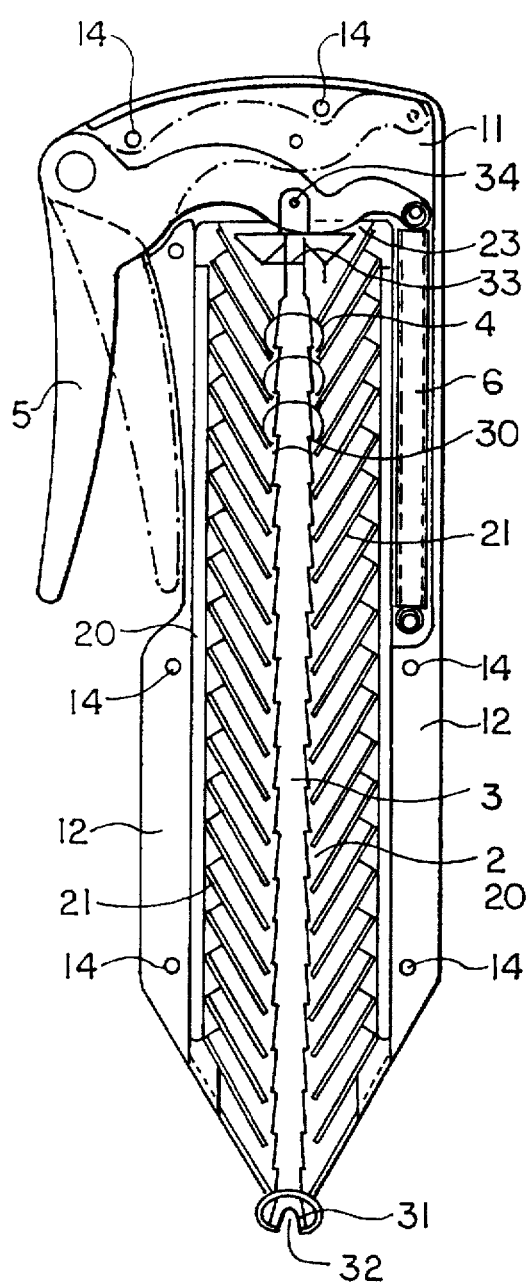
FIG. 2 shows the same device in FIG. 1 after removal of the front housing shell.

The more specific design of the device in the invention can be seen in FIG. 2, after removal of the front housing shell 10. Here we can see that at least the back housing shell 11 has reinforced side cheeks 12, which are so thick that they leave a shaft free between them that is wide enough to take the magazine 2. The magazine 2 consists of two side strips 20, on which there are retaining plates 21 running parallel to one another and pointing at an angle downward toward the center. The ends of two opposite spring-action retaining plates 21 approach one another up to a distance that is smaller than the shoulder width of the skin clip 4 to be held in the magazine. When the skin clips 4 move downward, this makes the two opposite retaining plates 21 bend elastically outward, while due to the reacting force of the skin clips upward, the spring plates act as locks, because the reaction forces are introduced into them more or less exactly in the longitudinal direction of the spring plates.

The two lateral strips 20, with the spring retaining plates 21 molded onto them can directly form one part of the reinforced side cheeks 12 or form a magazine 2 as an independent component via a common back wall 23. In the latter case, this component is closed with a front cover plate. A loaded magazine, the changeable part of the device, consequently consists of the two side strips 20 with the spring retaining plates 21 and the back wall 23 connecting the two strips and the cover plate 24, as well as a feed ratchet 3 that goes through the middle of the magazine in the longitudinal direction. The feed ratchet 3 is shaped like a sawtoothed, sword-shaped rod, whose bottom end where the skin clips are dispensed is widened. In the drawing, the saw teeth are marked 30, and the widening on the end 31. The widening 31 on the end itself has a curved recess 32. This recess is used to push the lowermost, spread-open skin clip over the edges of the wound curved upward. The top end of the feed ratchet 3 has a neck 33 with an attachment eye 34. The eye 34 is used to attach and detach the feed ratchet 3 to the lever arm of the actuating lever 5 inside. To change the magazine 2, the connection between the feed ratchet 3 and the actuating lever 5 need only be released, whereupon the whole magazine 2 can be changed.

Besides the preferred form of embodiment shown here, other designs of the magazine 2 are completely conceivable. Thus, it can suffice that the magazine 2 has only one strip 20 on one side with spring retaining plates 21. Another variation consists of the fact that one spring plate works alternately from the left and then from the right on two adjacent skin clips stacked in the magazine. This requires only a somewhat reinforced form of the spring plates 21. On the lever arm of the actuating lever 5 inside, a retaining spring 6 grasps the end. The retaining spring 6 is in a recess 13 in the reinforced side cheek 12.

Figure 6:
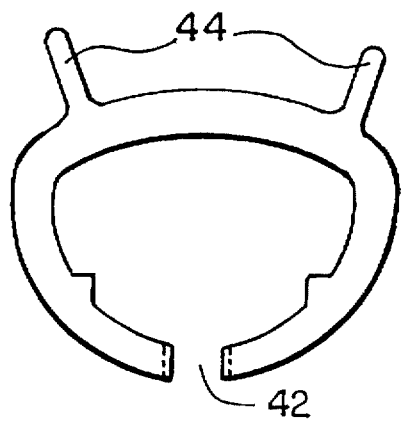
FIG. 6 shows again a slightly altered embodiment of the skin clip in a side view on the same scale as in FIG. 3.
Figure 4:
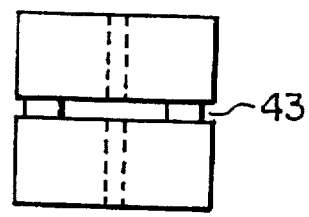
FIG. 4 shows a skin clip like those in FIG. 3 by itself in a top view on a somewhat smaller scale and FIG. 5 shows a variation of the skin clip in the same view as in FIG. 4, and lastly
Figure 5:
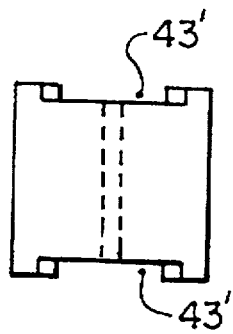

FIGS. 3–6 show various possible forms of embodiment of the skin clips used for the device in the invention. The skin clips used here are roughly in the form of a shell with a clamping gap 42 running longitudinally. The forms of embodiment of the skin clip 4 in FIGS. 3 and 4 also have a central guide 43 running perpendicular to the clamping gap. The feed ratchet 3 goes through this guide 43. Retaining ribs 41 pointing to the inside on the side legs act with the feed ratchet 3. The saw teeth 30 of the feed ratchet 3 are on the retaining ribs 43. Instead of the central guide 43, the skin clip 4 can also have lateral guides 43'. In this case, the device in the invention must then be made with two parallel feed ratchets 3 that run precisely parallel to one another corresponding to the width of the surgical clips. This variation is considered in claim 1, where at least one feed ratchet is mentioned. In principle, the edges of the wound in the clamping gap 42 shrink during healing, so that the surgical clips 4 can be plucked off with ease. But if the surgical clips need to be removed to check the wound, this can be done using a corresponding spreading forceps or the surgical clips 4 can have two retaining ribs 44 pointing laterally to the outside and up, as the example in FIG. 6 shows. These can be made so that stacking the skin clips on the feed ratchet 3 is not affected by this.

Figure 3:
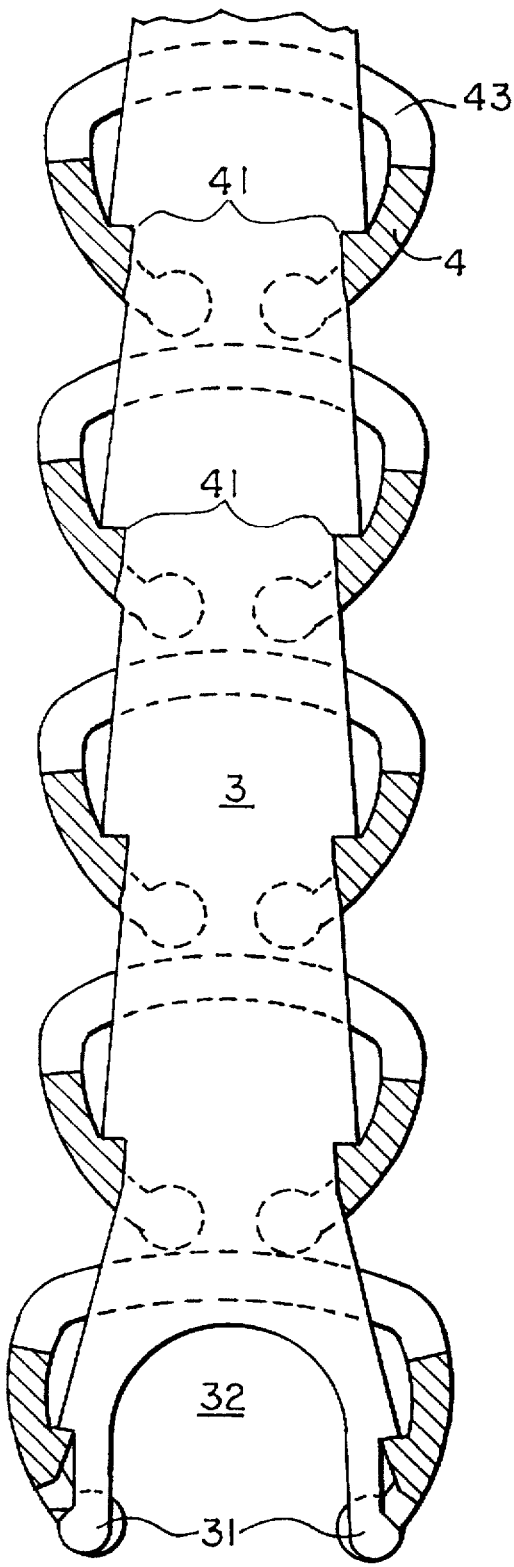
FIG. 3 shows the feed ratchet by itself with skin clips stacked on it, on an enlarged scale.

To activate the device in the invention, the user presses on the actuating lever 5. The arm of the actuating lever in the housing 1 is thereby moved upward and pulls the feed ratchet 3 up with it. The skin clips 4 stacked on the feed ratchet 3 are prevented by the spring plates 21 from making this movement too and thus remain on the same level while the feed ratchet moves up. FIG. 3 shows that consequently, the clips are removed from the saw teeth 30 and the clips are slightly splayed, until they are slid off over the next saw tooth 30 of the feed ratchet 3. Now, when the actuating lever 5 is released, the retaining spring 6 pulls the arm of the actuating lever 5 down and thus moves the feed ratchet 3 down too. Since the skin clips in turn now lie with their respective retaining ribs 41 behind the corresponding saw teeth 30 of the feed ratchet 3, they move down with it, and, at the same time, the spring retaining plates 21 bend outward. All the surgical clips on the feed ratchet are now one position lower than before, with the exception of the skin clip already at the bottom. That one is on the expanded part 31 and is spread so wide that the edges of the wound to be closed can easily be inserted into the spread-open clamping gap 42, which in this position corresponds roughly to the width of the curved recess 32 of the feed ratchet 3. When it is next activated, this lowest clip is pushed off the feed ratchet and springs back shut.

Since the device in the invention is no longer disposable, at least in terms of the housing and the activating device, this part is made of an especially resistant material, which can be sterilized many times. Thus these parts may be injection molded of aluminum, for example. But high-quality plastics can also be considered.

We claim:

1. A device for positioning skin clips comprising:
  a housing defining a longitudinal axis and having an opening at a lower end along the longitudinal axis; and
  a magazine disposed within the housing, the magazine comprising:
    a backstop ratchet comprising a plurality of spring retaining plates extending toward the longitudinal axis of the housing, and
    a feed ratchet comprising a sword-like rod disposed within the magazine along the central axis of the housing, a plurality of saw teeth formed on opposed sides of the rod, the feed ratchet having a widened lower end extending through the opening at the lower end of the housing, the feed ratchet axially movably attached to the housing for retraction and extension generally along the longitudinal axis with respect to the backstop ratchet;
  whereby skin clips retained on the saw teeth of the feed ratchet are prevented from movement away from the opening by the spring retaining plates upon retraction of the feed ratchet and are advanceable as a group toward the opening in the housing upon extension of the feed ratchet toward the opening, a lowermost one of the skin clips being spread open on the widened lower end of the feed ratchet upon advancement of the skin clips toward the opening.

2. The device of claim 1, wherein the backstop ratchet is integrally formed with the housing.

3. The device of claim 1, wherein the magazine is removably attached to the housing.

4. The device of claim 1, wherein the magazine comprises a plastic casing having a partially transparent portion.

5. The device of claim 1, wherein the backstop feed surrounds the feed ratchet.

6. The device of claim 1, further comprising an actuator movably mounted on the housing and attached to the feed ratchet for actuating movement of the feed ratchet generally along the longitudinal axis repetitively at least approximately a distance between two adjacent clips.

7. The device of claim 6, wherein the actuator comprises a lever biassed into a starting position.

8. The device of claim 6, wherein the feed ratchet is removably attached to the actuator.

* * * * *